US009636038B2

(12) United States Patent
Nonaka

(10) Patent No.: US 9,636,038 B2
(45) Date of Patent: May 2, 2017

(54) ELECTRICAL IMPEDANCE MEASURING APPARATUS

(71) Applicant: NIHON KOHDEN CORPORATION, Tokyo (JP)

(72) Inventor: Yukio Nonaka, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 130 days.

(21) Appl. No.: 14/625,336

(22) Filed: Feb. 18, 2015

(65) Prior Publication Data

US 2015/0238116 A1    Aug. 27, 2015

(30) Foreign Application Priority Data

Feb. 27, 2014   (JP) ................. 2014-037524

(51) Int. Cl.
| | | |
|---|---|---|
| F16L 25/00 | (2006.01) |
| A61B 5/053 | (2006.01) |
| A61B 5/00 | (2006.01) |
| A61B 5/08 | (2006.01) |

(52) U.S. Cl.
CPC ............ *A61B 5/0536* (2013.01); *A61B 5/004* (2013.01); *A61B 5/0809* (2013.01); *A61B 5/6823* (2013.01); *A61B 5/6832* (2013.01); *A61B 5/743* (2013.01); *A61B 5/7485* (2013.01); *A61B 5/0037* (2013.01); *A61B 2562/0214* (2013.01); *A61B 2562/046* (2013.01); *A61B 2576/02* (2013.01)

(58) Field of Classification Search
CPC .... A61B 5/0536; A61B 5/6823; A61B 5/6832
USPC ......................................................... 324/692
See application file for complete search history.

(56) References Cited

U.S. PATENT DOCUMENTS

| | | | |
|---|---|---|---|
| 4,539,640 A * | 9/1985 | Fry ...................... | A61B 5/0536 600/547 |
| 8,321,007 B2 | 11/2012 | Teschner et al. | |
| 2004/0092809 A1 | 5/2004 | DeCharms | |
| 2005/0105789 A1* | 5/2005 | Isaacs ................... | G06T 7/0004 382/141 |

(Continued)

OTHER PUBLICATIONS

A. De Groote, M. Wantier, G. Cheron, M. Estenne, M. Paiva, "Chest wall motion during tidal breathing", Journal of Applied Physiology Published Nov. 1, 1997 vol. 83 No. 5, 1531-1537.*

(Continued)

*Primary Examiner* — Thomas Valone
(74) *Attorney, Agent, or Firm* — Pearne & Gordon LLP

(57) ABSTRACT

An electrical impedance measuring apparatus includes: a plurality of electrodes adhered to a periphery of a chest; a potential measurer configured to perform a process of applying a current to any ones of the electrodes, and measuring potentials by means of other electrodes; an impedance acquirer, based on the applied current and the potentials measured by the potential measurer, configured to obtain an impedance of each of meshes, a chest section divided into the meshes; a histogram producer configured to set, in the chest section, at least one ROI including from a ventral side to a dorsal side, and configured to obtain a histogram of an impedance distribution in the ROI; and a producer configured to produce a color impedance distribution map in which amplitudes of the histogram are replaced with corresponding colors.

16 Claims, 7 Drawing Sheets

(56) References Cited

U.S. PATENT DOCUMENTS

2010/0198101 A1* 8/2010 Song .................. A61B 5/0536
600/547
2014/0012061 A1 1/2014 Song et al.

OTHER PUBLICATIONS

Stack Overflow, "How to Normalize a Histogram", http://stackoverflow.com/questions/5320677/how-to-normalize-a-histogram-in-matlab, p. 1-6, date: Aug. 8, 2011.*
Gunnar Elke et al.; "Quantification of ventilation distribution in regional lung injury by electrical impedance tomography and xenon computed tomography"; Physiological Measurement, Institute of Physics Publishing, Bristol, GB; vol. 34, No. 10, Sep. 11, 2013; pp. 1303-1318; XP020251547.
The extended European search report for the related European Patent Application No. 15155944.0 dated Jul. 3, 2015.

* cited by examiner

ELECTRICAL IMPEDANCE MEASURING APPARATUS

CROSS-REFERENCE TO RELATED APPLICATION(S)

This application is based upon and claims the benefit of priority from prior Japanese patent application No. 2014-037524, filed on Feb. 27 2014, the entire contents of which are incorporated herein by reference.

BACKGROUND

The presently disclosed subject matter relates to an electrical impedance measuring apparatus which is called the EIT (Electrical Impedance Tomography) or the like.

In the EIT, the impedance distribution of the chest is continuously displayed as a tomographic image, or, in place of or together with the tomographic image, an impedance variation waveform is displayed. In artificial ventilation therapy of respiratory disease such as ARDS (Acute Respiratory Distress Syndrome), a diagnosis is performed based on EIT images.

There is a related-art technique in which, in the EIT, the lung region in a tomographic image is segmented into several ROIs (Regions of Interest), and the ratio of the value of an impedance integration of an ROI to that of the all ROIs is displayed in the form of a waveform or a numerical value (see U.S. Pat. No. 8,321,007).

The EIT images show the aerated state of the lungs. In treatment of ARDS or the like, the state where aeration spreads over not only the ventral side but also the dorsal side is used as an index indicating a good state. Depending on the ratio of the value of an impedance integration of an ROI to that of the all ROIs which is obtained as disclosed in U.S. Pat. No. 8,321,007, however, it is difficult to intuitively know the spread of aeration from the ventral side to the dorsal side. Moreover, also depending on a tomographic image and impedance variation waveform in the EIT, it is difficult to know the spread of aeration from the ventral side to the dorsal side. Therefore, there is a need to develop an electrical impedance measuring apparatus which enables the spread of aeration from the ventral side to the dorsal side to be adequately known in a hyperextension state.

SUMMARY

The presently disclosed subject matter may provide an electrical impedance measuring apparatus having a configuration which enables the spread of aeration from the ventral side to the dorsal side to be adequately known.

The electrical impedance measuring apparatus may comprise: a plurality of electrodes which are adapted to be adhered to a periphery of a chest of a living body; a potential measurer which is configured to perform a process of applying a current to any ones of the electrodes, and measuring potentials by means of other electrodes, on all of the electrodes while changing the electrodes to which the current is to be applied; an impedance acquirer which, based on the applied current and the potentials measured by the potential measurer, is configured to obtain an impedance of each of meshes, a chest section divided into the meshes; a histogram producer which is configured to set, in the chest section, at least one ROI including from a ventral side to a dorsal side, and which is configured to obtain a histogram of an impedance distribution in the ROI; and a producer which is configured to produce a color impedance distribution map in which amplitudes of the histogram are replaced with corresponding colors.

The histogram producer may obtain a normalized histogram, and the producer may produce a color impedance distribution map in which amplitudes of the normalized histogram are replaced with corresponding colors.

The electrical impedance measuring apparatus may further comprise: a display controller which is configured to cause the color impedance distribution map to be displayed.

The display controller may further cause the histogram of the impedance distribution to be displayed.

The display controller may cause color impedance distribution maps to be displayed while being arranged in a direction of a time axis.

The histogram producer may set two ROIs, a lung field laterally segmented into the ROIs, and obtain histograms of impedance distributions in the ROIs, and the producer may produce color impedance distribution maps in which amplitudes of the histograms of the impedance distributions are replaced with corresponding colors.

The electrical impedance measuring apparatus may further comprise: a centroid calculator which is configured to obtain a centroid of the impedance distribution in the ROI. The display controller causes the centroid to be displayed.

The electrical impedance measuring apparatus may further comprise: a curve producer which is configured to produce a displacement curve of a centroid, the displacement curve connecting together centroids of impedance distributions that vary with time in the ROI. The display controller may cause the displacement curve to be displayed.

The centroid calculator may set two ROIs, a lung field laterally segmented into the ROIs, and further obtain centroids of impedance distributions in the ROIs, and the display controller may cause the centroids to be displayed.

The curve producer may set two ROIs, a lung field laterally segmented into the ROIs, and further obtain displacement curves of centroids, the displacement curves connecting together centroids of impedance distributions that vary with time in the ROIs, and the display controller may cause the displacement curves to be displayed.

DETAILED DESCRIPTION OF EXEMPLARY EMBODIMENTS

Figure 1:
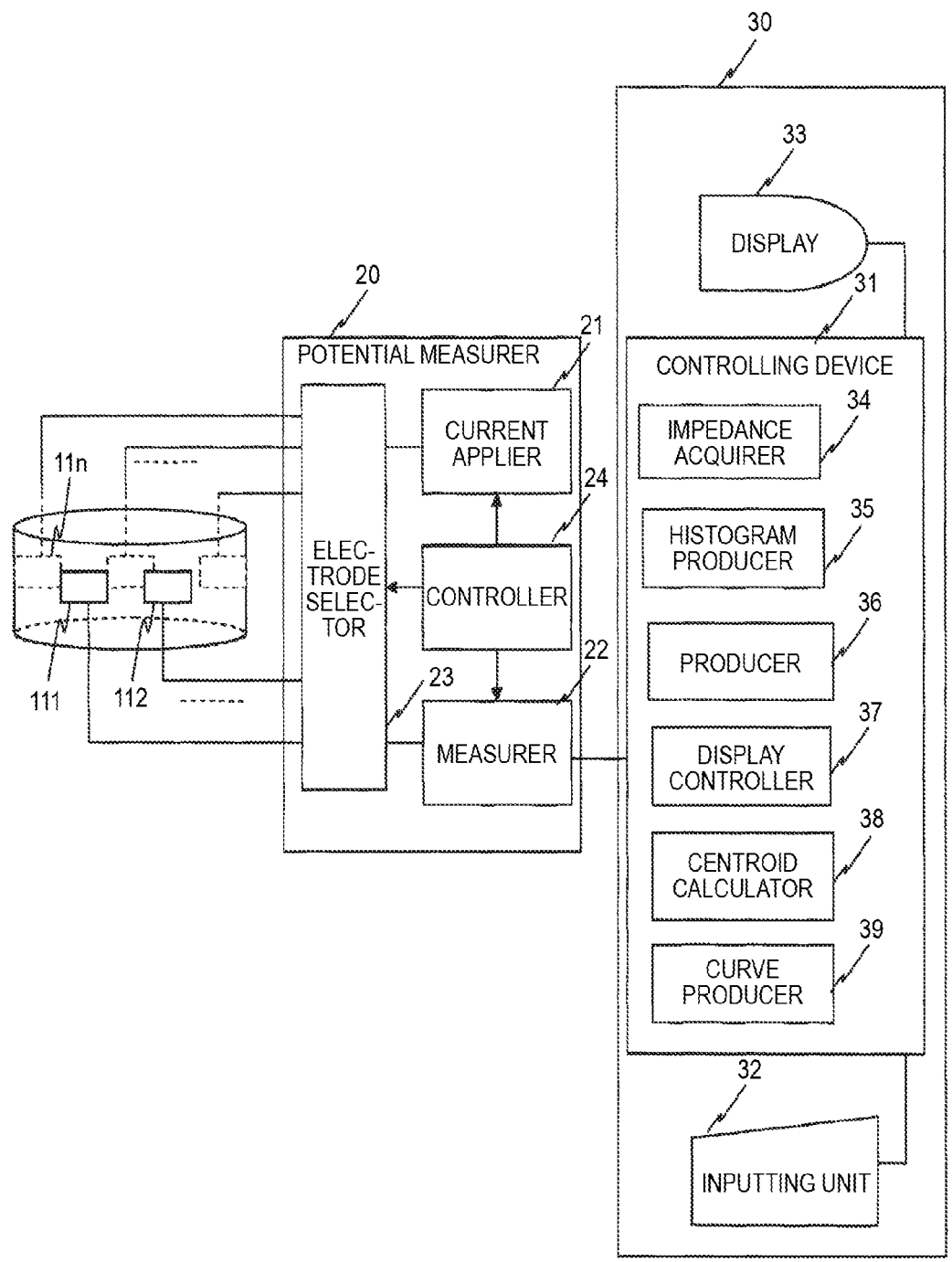
FIG. 1 is a functional block diagram of an embodiment of the electrical impedance measuring apparatus of the presently disclosed subject matter.

Hereinafter, an embodiment of the electrical impedance measuring apparatus of the presently disclosed subject matter will be described with reference to the accompanying drawings. In the figures, the identical components are denoted by the same reference numerals, and duplicate description is omitted. FIG. 1 is a diagram of the embodiment of the electrical impedance measuring apparatus of the presently disclosed subject matter. The electrical impedance measuring apparatus mainly includes a plurality of electrodes 111 to 11n, a potential measurer 20, and a computer 30.

The plurality of electrodes 111 to 11n are to be adhered to the periphery of the chest of the living body. For example, a necessary number of electrodes are used at the same height and at regular intervals. The potential measurer 20 includes a current applier 21, a measurer 22, an electrode selector 23, and a controller 24. Based on the control of the controller 24, the current applier 21 applies a current to electrode pairs which are connected to the current applier 21 via the electrode selector 23. The measurer 22 measures potentials produced in the electrode pairs, based on the control of the controller 24.

In accordance with the control of the controller 24, the electrode selector 23 connects the first electrode pair to which the current is to be applied, to the current applier 21, and the electrode pairs which are not connected to the current applier 21, to the measurer 22, so that the potential can be measured under this state. Then, the potential measurement is performed. Next, the electrode pair which is connected to the measurer 22 is changed to another pair so that the potential can be measured. Then, the potential measurement is performed. Thereafter, the all electrode pairs other than the first electrode pair to which the current is applied are sequentially connected to the measurer 22, and subjected to the potential measurement.

In accordance with the control of the controller 24, next, the electrode selector 23 connects the second electrode pair to which the current is to be applied, to the current applier 21, and the electrode pairs which are not connected to the current applier 21, to the measurer 22, so that the potential can be measured under this state. Then, the potential measurement is performed. Thereafter, the all electrode pairs other than the second electrode pair to which the current is applied are sequentially connected to the measurer 22, and subjected to the potential measurement. Next, the third electrode pair to which the current is to be applied is selected, and the potential measurement is performed in a manner similar to the above. Thereafter, all the electrodes 111 to 11n are similarly sequentially selected as the electrode pair to which the current is to be applied, the all electrode pairs other than the electrode pair to which the current is applied are sequentially connected to the measurer 22, and the potential measurement is performed.

The computer 30 has a controlling device 31 which functions as a calculator having a CPU and a memory, and an inputting unit 32 and a display 33 which are connected to the controlling device 31. Command and various kinds of information are input through the inputting unit 32. The display 33 displays various kinds of display information such as an EIT image, various waveforms, numerical values, and characters.

The controlling device 31 includes an impedance acquirer 34, a histogram producer 35, a display controller 37, a centroid calculator 38, and a curve producer 39. The impedance acquirer 34 obtains the impedance of each of meshes which are obtained by dividing a chest section region into meshes, based on the applied current and the potentials obtained by the potential measurer 20. Namely, the impedances of the meshes which are obtained by dividing a chest section region into meshes are obtained by using a related-art conversion table based on the applied current and the obtained potentials. The meshes correspond to the pixels of the EIT image, respectively. An image in which each of the meshes is converted to a color corresponding to the impedance can be displayed as an EIT image.

Figure 2:
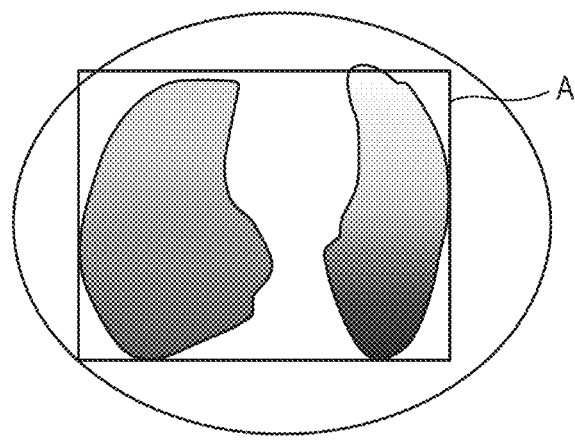
FIG. 2 is a view showing one ROI in the case where the one ROI is set from the ventral side of a chest section to the dorsal side.

The histogram producer 35 sets one or more ROIs including from the ventral side to the dorsal side in the chest section, and obtains a histogram of the impedance distribution in the ROIs. As shown in FIG. 2, an ROI A may be set in which the whole region of the chest section is one ROI. As shown FIG. 3, alternatively, the lung field in the whole region of the chest section may be laterally segmented into two ROIs AR, AL, so that the impedance distribution between the ventral side and the dorsal side can be displayed in detail.

An ROI is divided into a plurality of meshes, and the impedances which are obtained by the impedance acquirer 34 are made correspond to the meshes, respectively. In the case where the whole of the ROI A in FIG. 2 contains, for example, n×m meshes, impedance values are allocated to the n×m meshes, respectively. Here, n indicates the number of meshes of one row contained from one side of the body to the other side, and m indicates the number of meshes of one column contained from the ventral side of the body to the dorsal side in the ROI A. The impedance values are divided into an N (integer) number of hierarchies, the hierarchy values are added together in the row direction, and a histogram of the impedance distribution in the column direction can be obtained. In this way, the histogram producer obtains a normalized histogram. As a result, a normalized histogram can be obtained as shown in, for example, (a) of FIG. 4.

Figure 5:
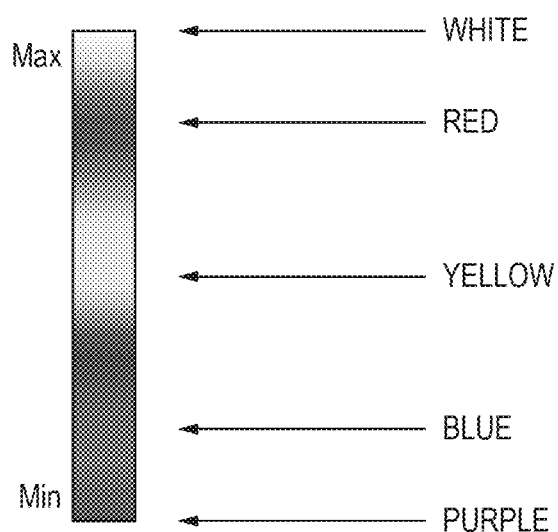
FIG. 5 is a view showing an example of correspondence relationships between amplitudes of a histogram of an ROI which is produced by the electrical impedance measuring apparatus of the embodiment of the presently disclosed subject matter, and colors to which the amplitudes are to be converted.

A producer 36 produces a color impedance distribution map in which the amplitudes of the normalized histogram are replaced with corresponding colors. As shown in FIG. 5, for example, colors can be correspondingly allocated to the amplitudes. Namely, the color allocation can be performed in a following manner. White is allocated to the maximum amplitude (MAX). In accordance that the amplitude becomes lower, the color gradually approaches red. In accordance that the amplitude further becomes lower, the color gradually approaches yellow. In accordance that the amplitude still further becomes lower, the color gradually approaches green. In accordance that the amplitude still further becomes lower, the color gradually approaches blue. Purple is allocated to the minimum amplitude (MIN).

Figure 4:
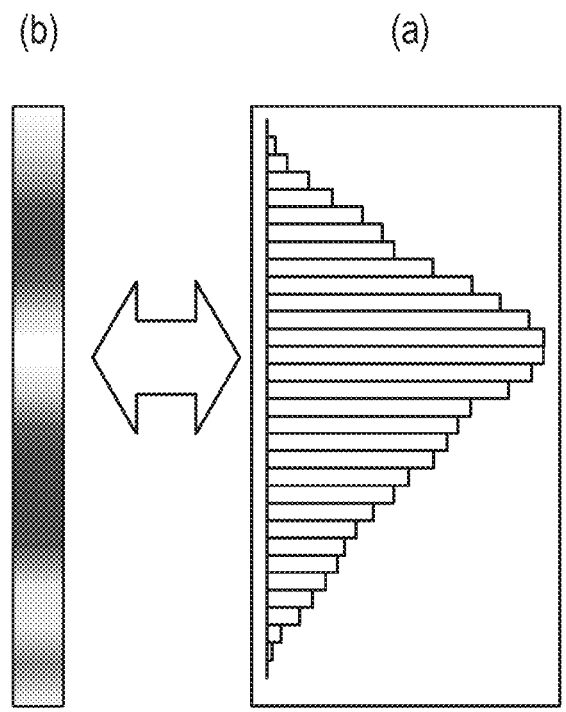
FIG. 4 is a view showing an example of a histogram of one ROI which is produced by the electrical impedance measuring apparatus of the embodiment of the presently disclosed subject matter, and a color impedance distribution map corresponding to the histogram.

When the above-described color allocation is performed on the histogram of (a) of FIG. 4, the resulting distribution map is as shown in (b) of FIG. 4. In the histogram of (a) of FIG. 4, the amplitude is high in the vicinity of the middle, and, the more approaching the both ends, the lower amplitude is. Therefore, the color impedance distribution map is produced so that the vicinity of the middle is white corresponding to the maximum amplitude, the color gradually becomes red when the position advances toward the both ends of the white area, the color approaches yellow when the position further advances toward the ends, and the color approaches green when the position still further advances from that of yellow to the ends. When the processes from the potential measurement to the production of the color impedance distribution map are performed at predetermined time intervals, color impedance distribution maps are produced in time series.

The display controller 37 causes the color impedance distribution maps which are produced as described above, to be displayed on the display 33. The color impedance distribution maps can be displayed while being arranged in the direction of the time axis. The display controller 37 may be configured so as to further display the histogram of an impedance distribution.

Based on a histogram of the impedance distribution, the centroid calculator 38 of the controlling device 31 obtains the centroid of the impedance distribution in an ROI. The centroid of a histogram is equal to the average value of the histogram, and may be obtained as the average value of impedances of meshes in the ROI.

Figure 3:
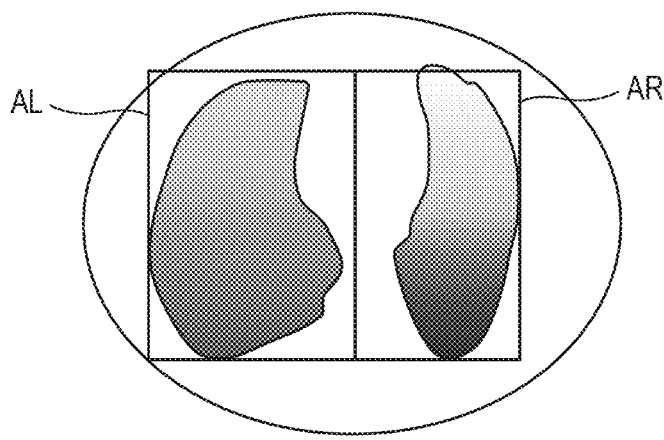
FIG. 3 is a view showing ROIs in the case where the lung field is laterally segmented into two ROIs from the ventral side of a chest section to the dorsal side.

When the centroid of the impedance distribution is obtained, one centroid (impedance value) is obtained in the embodiment of FIG. 2 in which the one ROI is set, and two centroids (impedance values) are obtained in the embodiment of FIG. 3 in which the two ROIs are set.

The curve producer 39 produces a displacement curve of the centroid which is obtained by connecting together the centroids that vary with time in the ROIs. The display controller 37 can cause the displacement curve of the centroid to be displayed. The centroid calculator 38 sets two ROIs which are obtained by laterally segmenting the lung field, and obtains the centroid of the impedance distribution in the ROIs, and the display controller 37 causes the centroid to be displayed.

Figure 6:
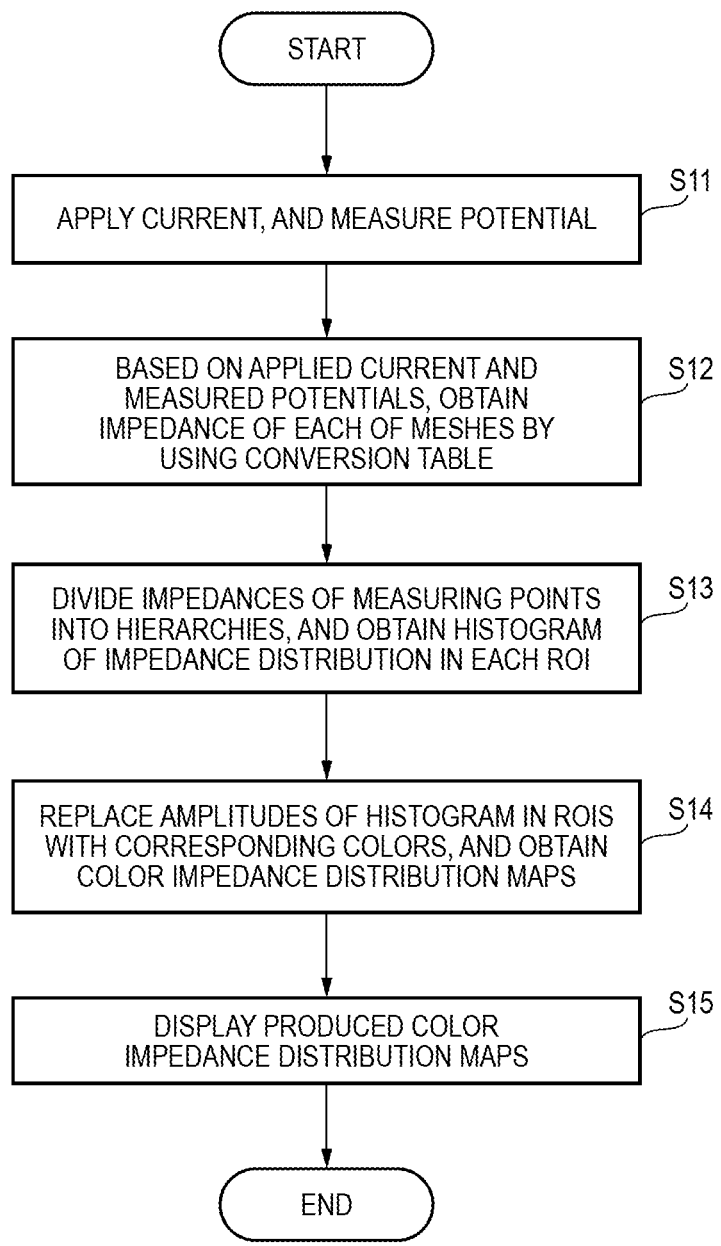
FIG. 6 is a flowchart illustrating the operation of producing a color impedance distribution map by the electrical impedance measuring apparatus of the embodiment of the presently disclosed subject matter.

When a color impedance distribution map is to be displayed in the thus configured electrical impedance measuring apparatus, the apparatus operates as shown in the flowchart of, for example, FIG. 6. The operation will be described. First, the plurality of electrodes 11 1 to 11 n are adhered to the periphery of the chest of the living body, and the measurement is started. An electrode pair is selected, and a current is applied to the selected electrode pair. The potentials are obtained from the electrode pairs to which the current is not applied. The potentials are measured while sequentially changing electrodes from which the potential is to be obtained. When the potential measurement is completed with respect to the all electrode pairs to which the current is not applied, the electrode pair to which the current is to be applied is changed to another electrode pair, and the subsequent potential measurement will be performed in a similar manner. In this way, the measurement is continued until the current apply is performed on the all electrode pairs, and the corresponding potential measurement is completed. Then, the series of potential measurements is ended (S11).

Based on the applied current and the measured potentials, next, the impedance of each of meshes is obtained by using the related-art conversion table (S12). By using the impedances of the meshes, for each of the ROIs, the impedance values are divided into the N (integer) number of hierarchies, and a histogram of the impedance distribution in the column direction (from the ventral side to the dorsal side) in the ROI is obtained (S13). For each of the ROIs, next, a color impedance distribution map in which the amplitudes of the histogram are replaced with corresponding colors is produced (S14), and the produced color impedance distribution map is displayed (S15).

Figure 7:
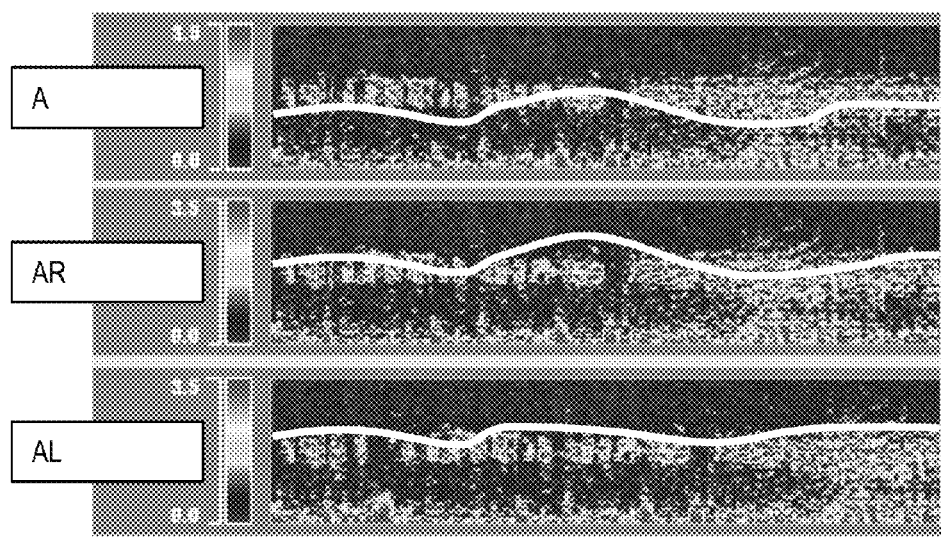
FIG. 7 is a view showing a display example of a color impedance distribution map produced by the electrical impedance measuring apparatus of the embodiment of the presently disclosed subject matter.

FIG. 7 shows an example in which, as a result of the operation of step S15, color impedance distribution maps of the ROI A in FIG. 2 and the ROIs AR, AL in FIG. 3 are displayed in time series and in a trend format. The display may be performed on one screen, or the ROI A in FIG. 2 and the ROIs AR, AL in FIG. 3 may be selectively displayed on another screen. In each ROI, the higher the position in the figure, the lower the impedance, and the lower the position in the figure, the higher the impedance. A higher impedance indicates a more highly aerated state. Therefore, it can be determined that, when the color of the lower side of the figure is white or red, higher aeration is attained. When the trend display of a color impedance distribution map is visually checked in this way, the spread of aeration from the ventral side to the dorsal side can be known intuitively and adequately.

Figure 8:
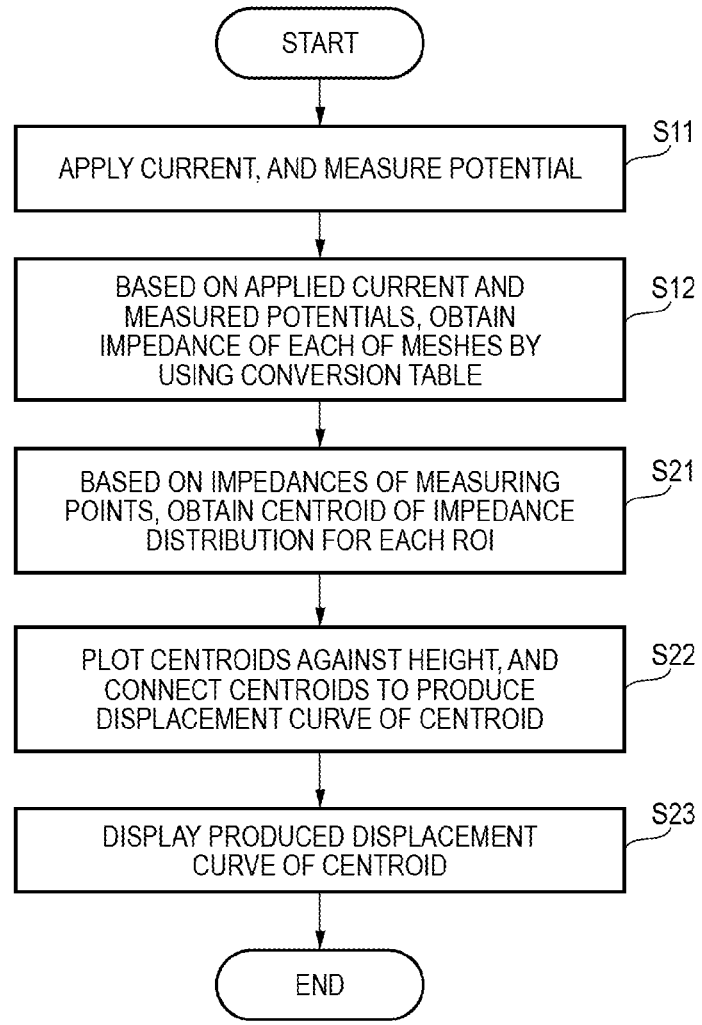
FIG. 8 is a flowchart illustrating the operation of producing a displacement curve of the centroid by the electrical impedance measuring apparatus of the embodiment of the presently disclosed subject matter.

When a displacement curve of the centroid is to be displayed in the thus configured electrical impedance measuring apparatus, the apparatus operates as shown in the flowchart of, for example, FIG. 8. The operation will be described. Steps 11 and 12 are identical with those of the flowchart of FIG. 6 for displaying a color impedance distribution map. After step S12, by using the impedances of the meshes in the all ROIs, the centroid of the impedance distribution is obtained for each of the ROIs (S21). Next, the centroids of the ROIs which are obtained in step S21 above are plotted against the height (amplitude), and connected together in time series to produce a displacement curve of the centroid (S22). The produced displacement curve of the centroid is displayed (S23).

Figure 9:
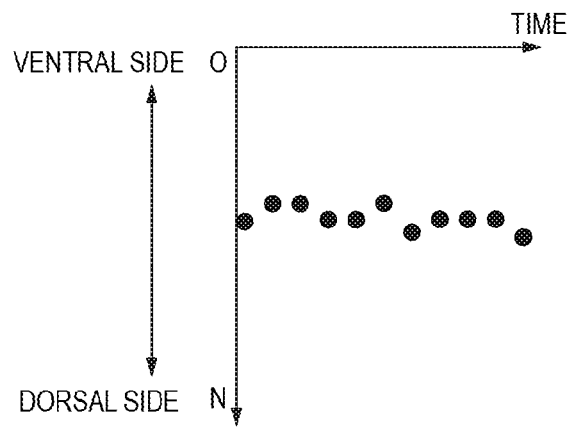
FIG. 9 is a view showing a result of acquisition of the centroid of the impedance distribution produced by the electrical impedance measuring apparatus of the embodiment of the presently disclosed subject matter.
Figure 10:
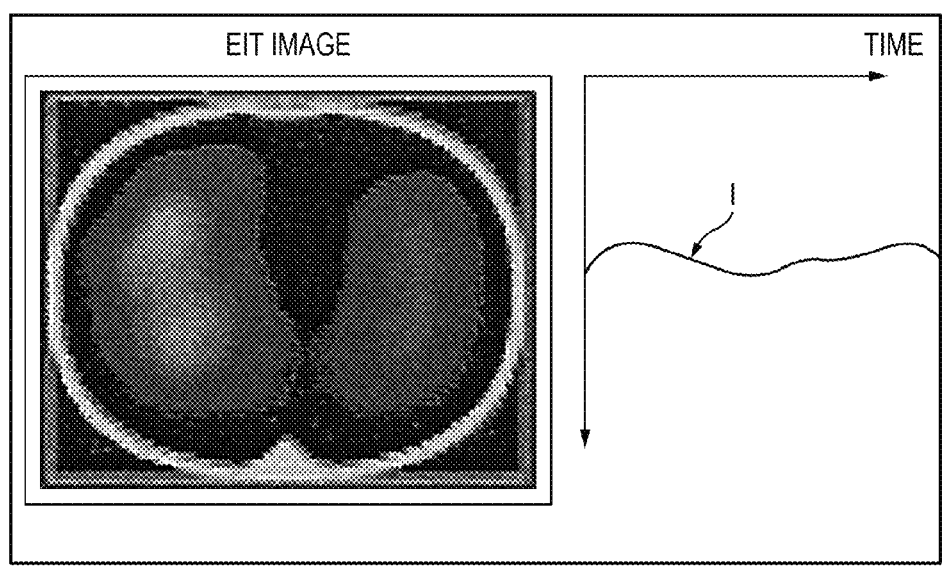
FIG. 10 is a view showing a display example of the displacement curve of the centroid produced by the electrical impedance measuring apparatus of the embodiment of the presently disclosed subject matter.

When, in step S21, it is assumed that one column extending from the ventral side to the dorsal side is configured by meshes as shown in FIG. 9, for example, the centroids (indicated by solid points) of the impedance distribution in one ROI are obtained in time series. Then, the centroids are connected in time series, and a displacement curve of the centroid 1 such as shown in FIG. 10 can be produced. The display controller 37 causes the displacement curve of the centroid 1 which is produced as described above, to be displayed on the display 33. The display controller 37 can cause the displacement curve of the centroid 1 to be displayed together with an EIT image as shown in FIG. 10. In FIG. 7, the displacement curve of the centroid is displayed by one line in the direction of the time axis. The curve may be displayed together with a trend display of a color impedance distribution map in the time series direction. In the display of FIG. 10, from the EIT image, the aerated state from the ventral side to the dorsal side in the chest can be known, and, from the displacement curve of the centroid 1, it is possible to know intuitively and adequately how the centroid of impedances is displaced with time from the ventral side to the dorsal side, and how the aerated state varies.

According to the electrical impedance measuring apparatus of the presently disclosed subject matter, one or more ROIs including from the ventral side to the dorsal side are set in a chest section, a histogram of the impedance distribution in the ROIs is obtained, a color impedance distribution map in which amplitudes of the histogram are replaced with corresponding colors is produced, and the color impedance distribution map is displayed in a trend format. Therefore, the histogram of the impedance distribution in the one or more ROIs including from the ventral side of the chest section to the dorsal side can be intuitively known based on the colors, and the spread of aeration from the ventral side to the dorsal side can be adequately known.

What is claimed is:

1. An electrical impedance measuring apparatus comprising:
   a plurality of electrodes which are adapted to be adhered to a periphery of a chest of a living body;
   a potential measurer which is configured to perform a process of applying a current to any ones of the electrodes, and measuring potentials by means of other electrodes, on all of the electrodes while changing the electrodes to which the current is to be applied;
   an impedance acquirer which, based on the applied current and the potentials measured by the potential measurer, is configured to obtain an impedance of each of a plurality of meshes, a chest section being divided into the meshes;
   a histogram producer which is configured to set, in the chest section, at least one region of interest (ROI) including a region from a ventral side to a dorsal side, and which is configured to obtain a histogram of an impedance distribution in the ROI;
   a producer which is configured to produce a color impedance distribution map in which amplitudes of the histogram are replaced with corresponding colors;
   a curve producer which is configured to produce a displacement curve of a centroid, the displacement curve connecting together centroids of impedance distributions that vary with time in the ROI; and
   a display controller which is configured to cause the displacement curve to be displayed.

2. The electrical impedance measuring apparatus according to claim 1, wherein
   the histogram producer obtains a normalized histogram, and
   the producer produces a color impedance distribution map in which amplitudes of the normalized histogram are replaced with corresponding colors.

3. The electrical impedance measuring apparatus according to claim 1, wherein the display controller is configured to cause the color impedance distribution map to be displayed.

4. The electrical impedance measuring apparatus according to claim 3, wherein the display controller further causes the histogram of the impedance distribution to be displayed.

5. The electrical impedance measuring apparatus according to claim 3, wherein the display controller causes color impedance distribution maps to be displayed while being arranged in a direction of a time axis.

6. The electrical impedance measuring apparatus according to claim 1, wherein
   the histogram producer sets two ROIs, a lung field being laterally segmented into the ROIs, and obtains histograms of impedance distributions in the ROIs, and
   the producer produces color impedance distribution maps in which amplitudes of the histograms of the impedance distributions are replaced with corresponding colors.

7. The electrical impedance measuring apparatus according to claim 1, wherein
   a centroid calculator sets two ROIs, a lung field being laterally segmented into the ROIs, and further obtains centroids of impedance distributions in the ROIs, and
   the display controller causes the centroids to be displayed.

8. The electrical impedance measuring apparatus according to claim 1, wherein
   the curve producer sets two ROIs, a lung field being laterally segmented into the ROIs, and further obtains displacement curves of centroids, the displacement curves connecting together centroids of impedance distributions that vary with time in the ROIs, and
   the display controller causes the displacement curves to be displayed.

9. An electrical impedance measuring apparatus comprising:
   a plurality of electrodes which are adapted to be adhered to a periphery of a chest of a living body;
   a potential measurer which is configured to perform a process of applying a current to any ones of the electrodes, and measuring potentials by means of other electrodes, on all of the electrodes while changing the electrodes to which the current is to be applied;
   an impedance acquirer which, based on the applied current and the potentials measured by the potential measurer, is configured to obtain an impedance of each of a plurality of meshes, a chest section being divided into the meshes;
   a histogram producer which is configured to set, in the chest section, at least one region of interest (ROI) including a region from a ventral side to a dorsal side, and which is configured to obtain a histogram of an impedance distribution in the ROI;
   a producer which is configured to produce a color impedance distribution map in which amplitudes of the histogram are replaced with corresponding colors;
   a centroid calculator which is configured to obtain a centroid of the impedance distribution in the ROI; and
   a display controller which is configured to cause the centroid to be displayed.

10. The electrical impedance measuring apparatus according to claim 9, further comprising: a curve producer which is configured to produce a displacement curve of a centroid, the displacement curve connecting together centroids of impedance distributions that vary with time in the ROI, wherein the display controller causes the displacement curve to be displayed.

11. The electrical impedance measuring apparatus according to claim 9, wherein
   the centroid calculator sets two ROIs, a lung field being laterally segmented into the ROIs, and further obtains centroids of impedance distributions in the ROIs, and
   the display controller causes the centroids to be displayed.

12. The electrical impedance measuring apparatus according to claim 9, wherein
   the histogram producer obtains a normalized histogram, and the producer produces a color impedance distribution map in which amplitudes of the normalized histogram are replaced with corresponding colors.

13. The electrical impedance measuring apparatus according to claim 9, wherein the display controller is configured to cause the color impedance distribution map to be displayed.

14. The electrical impedance measuring apparatus according to claim 13, wherein the display controller is configured to cause the histogram of the impedance distribution to be displayed.

15. The electrical impedance measuring apparatus according to claim 13, wherein the display controller is configured to cause color impedance distribution maps to be displayed while being arranged in a direction of a time axis.

16. The electrical impedance measuring apparatus according to claim 9, wherein
the histogram producer sets two ROIs, a lung field being laterally segmented into the ROIs, and obtains histograms of impedance distributions in the ROIs, and
the producer produces color impedance distribution maps in which amplitudes of the histograms of the impedance distributions are replaced with corresponding colors.

* * * * *